United States Patent
Sigurdsson et al.

(10) Patent No.: US 11,227,249 B2
(45) Date of Patent: Jan. 18, 2022

(54) METHOD OF PROVIDING FEEDBACK DATA INDICATING QUALITY OF FOOD PROCESSING PERFORMED BY AN OPERATOR

(71) Applicant: MAREL ICELAND EHF, Gardabaer (IS)

(72) Inventors: Bjarni Sigthor Sigurdsson, Hafnarfjordur (IS); Gunnar Atli Thoroddsen, Reykjavík (IS); Sigurdur Halldor Adalsteinsson, Reykjavik (IS); Stella Gudjonsdottir, Reykjavík (IS); Thomas Thorsteinsson, Kopavogi (IS); Throstur Snaer Eidsson, Kopavogur (IS)

(73) Assignee: MAREL ICELAND EHF, Gardabaer (IS)

( * ) Notice: Subject to any disclaimer, the term of this patent is extended or adjusted under 35 U.S.C. 154(b) by 0 days.

(21) Appl. No.: 16/972,488

(22) PCT Filed: Jun. 4, 2019

(86) PCT No.: PCT/EP2019/064541
§ 371 (c)(1),
(2) Date: Dec. 4, 2020

(87) PCT Pub. No.: WO2019/234054
PCT Pub. Date: Dec. 12, 2019

(65) Prior Publication Data
US 2021/0256449 A1    Aug. 19, 2021

(30) Foreign Application Priority Data
Jun. 6, 2018    (EP) .................................... 18176282

(51) Int. Cl.
*G06K 9/00*        (2006.01)
*G06Q 10/06*       (2012.01)
(Continued)

(52) U.S. Cl.
CPC ....... *G06Q 10/06395* (2013.01); *A22B 5/007* (2013.01); *A22C 17/008* (2013.01);
(Continued)

(58) Field of Classification Search
CPC .................................................. A22C 17/008
See application file for complete search history.

(56) References Cited

U.S. PATENT DOCUMENTS

| 5,428,657 A | 6/1995 | Papanicolopoulos et al. |
| 7,976,368 B2 * | 7/2011 | Haucke ................. A22C 25/18 452/184 |

(Continued)

FOREIGN PATENT DOCUMENTS

| EP | 0361625 A2 | 4/1990 |
| WO | 2008102148 A1 | 8/2008 |

(Continued)

OTHER PUBLICATIONS

Extended European Search Report from corresponding Application No. EP18176282.4, dated Dec. 5, 2018.

(Continued)

*Primary Examiner* — Hadi Akhavannik
(74) *Attorney, Agent, or Firm* — Workman Nydegger

(57) ABSTRACT

A method and a system provide a feedback data indicating quality of a food processing performed by an operator. The method and system involve acquiring at least one image data of a food product from an operator; and processing the acquired image data. The processing includes detecting whether undesired objects are present in the food product, obtaining, in case undesired objects are detected, position (Continued)

data of the undesired objects within the food product, and utilizing the position data in issuing a feedback indicator indicating a position where the detected undesired objects are present within the food product processed by the operator.

17 Claims, 2 Drawing Sheets

(51) Int. Cl.
    *G06T 7/70*         (2017.01)
    *A22B 5/00*         (2006.01)
    *A22C 17/00*       (2006.01)
    *B65G 43/00*       (2006.01)
    *G06Q 50/04*       (2012.01)
    *G06T 7/00*         (2017.01)
    *G07C 3/14*         (2006.01)
    *G06F 3/14*         (2006.01)

(52) U.S. Cl.
    CPC .......... *A22C 17/0093* (2013.01); *B65G 43/00* (2013.01); *G06Q 50/04* (2013.01); *G06T 7/0004* (2013.01); *G06T 7/70* (2017.01); *G07C 3/146* (2013.01); *G06F 3/14* (2013.01); *G06T 2200/04* (2013.01); *G06T 2207/10116* (2013.01); *G06T 2207/30128* (2013.01)

(56) References Cited

U.S. PATENT DOCUMENTS

| | | | |
|---|---|---|---|
| 10,845,319 B2* | 11/2020 | Davis, III | G01N 33/12 |
| 2003/0098409 A1 | 5/2003 | Bond et al. | |
| 2010/0119038 A1* | 5/2010 | Suyama | G01V 5/0041 378/57 |
| 2014/0079291 A1* | 3/2014 | Johnson | G06T 7/0008 382/110 |
| 2014/0170947 A1* | 6/2014 | Sigurosson | G01N 23/083 452/184 |
| 2017/0205385 A1* | 7/2017 | Prystupa | A22C 17/0073 |
| 2019/0000094 A1* | 1/2019 | Hjalmarsson | B25J 9/0051 |

FOREIGN PATENT DOCUMENTS

| | | | |
|---|---|---|---|
| WO | 2011095998 A1 | 8/2011 | |
| WO | WO 2014/079448 A1 * | 5/2014 | |
| WO | 2017174768 A1 | 10/2017 | |

OTHER PUBLICATIONS

International Search Report and Written Opinion from corresponding PCT Application No. PCT/EP2019/064541, dated Sep. 9, 2019.

* cited by examiner

METHOD OF PROVIDING FEEDBACK DATA INDICATING QUALITY OF FOOD PROCESSING PERFORMED BY AN OPERATOR

FIELD OF THE INVENTION

The present invention relates to method and a system for providing feedback data indicating quality of food processing performed by an operator.

BACKGROUND OF THE INVENTION

Manually processing food products such as fish fillets is a challenging task, especially for food products where it may be difficult to visually detect undesired objects such as bones and cartilages.

In processing plants today, operators that process food products are provided with limited, if any, feedback about the quality of the processing. In fish factories as an example, it may be that the processing plant gets feedback from a customer that that quality of the overall food processing was not good enough.

In some cases, such fish factories may utilize X-ray apparatus to make quality checks to see if e.g. all bones were removed or not. If not, the fish fillets are rejected and typically recirculated into the system. However, individual operators will not be notified about whether or not improvement in the processing is needed.

SUMMARY OF THE INVENTION

On the above background it is an object of embodiments of the present invention to provide a method and a system which is capable of providing feedback data indicating the quality of the food processing.

In general, the invention preferably seeks to mitigate, alleviate or eliminate one or more of the above mentioned disadvantages of the prior art singly or in any combination. In particular, it may be seen as an object of embodiments of the present invention to provide a feedback method and a system that solves the above mentioned problems, or other problems.

To better address one or more of these concerns, in a first aspect of the invention, a method is provided for providing feedback data indicating quality of food processing, comprising: acquiring at least one image data of a processed food product (407) from an operator, processing the acquired image data, the processing including:
  detecting whether undesired objects are present in the processed food product,
  obtaining, in case undesired objects are detected, position data of the undesired objects within the processed food product,
utilizing the position data in issuing a feedback indicator indicating a position where said detected undesired objects are present within the food product processed by said operator.

Accordingly, a method is provided where it is now possible to indicate feedback data about the quality of the food processing. This means that an operator as an example may be directly informed about where improvements are needed in the food processing. More importantly, the operator may be informed where within the food object such improvements are needed which facilitates the improvement for the operator greatly. If the food object is e.g. a fish fillet, the operator may be informed that e.g. within the pin bone area of the fish fillets, improvements are needed in order to remove all the pin bones.

The feedback data may also be issued to e.g. a plant manager so as to allow the plant manager to have an overview over quality of the food processing for all or individual operators.

The term undesired objects may according to the present invention be understood as any objects that are not desirable toward consumers, such as, but not limited to, bones, cartilages, undesired surface tissues.

The food object may be selected from, but is not limited to, fish fillets, poultry meat, beef, pork, lamb.

The acquiring of at least one image data may particularly comprise the step of obtaining an electronic data file representing the image, e.g. obtained by X-ray, laser scanner, or digital camera.

The processing may particularly comprise the step of reading the electronic data file into a computer processing unit and using the computer processing unit and a predefined computer program to detect the undesired objects and to determine the position data.

The feedback indicator may be generated by the computer processing unit.

In one embodiment, said feedback data is visually shown to the operator via a display. In an embodiment, this may visually be shown within outlines of a food product being processed. As an example, if the food product is fish fillets, outlines of a fish fillet may be shown on the screen and the feedback indicator may be illustrated within the correct area within the outlines of the fish fillet so as to allow the operator to immediately know where he/she needs to improve the processing. An image of the actual, or similar, food product that was processed, e.g. said fish fillet, may also be shown with said feedback indicator instead of said outlines.

In one embodiment, in case undesired objects are detected in a subsequent processed food product processed by said operator, where the undesired objects are positioned within the same or similar position as for said processed food product, an intensifier is triggered indicating an increase in magnitude of said feedback indicator. In that way, it is possible to indicate repetitive failures in the food processing. Referring to said example, if the operator again in a subsequent fish fillet does not remove all the pin bones, the operator (or e.g. said plant manager) is informed about repetitive failures in that area. Based thereon, the plant manager may e.g. be able to plan additional training for this operator and other operators.

The term "subsequent processed food product" may, in one embodiment, be defined such that two products either directly one after the other in a row of food products or within a certain distance in place or time after the other has the same error. By same error is meant same kind of undesired object or an undesired object in the same location or substantially in the same location.

"Within a certain distance in place" may indicate a number of other food products which can be between the two food products having the same error. In one example, the number may be zero indicating that the magnitude is increased when two directly adjacent food products have the same error. In another example, the number is 10 indicating that the magnitude is increased when two products in a row of ten products have the same error.

"Within a certain distance in time" may indicate a duration in which two food products are experienced with the same error. In one example, the duration may be 30 seconds indicating that the magnitude is increased when two food products have the same error in a period of 30 seconds. In another example, the duration is 2 minutes indicating that the magnitude is increased when two products within a period of 2 minutes have the same error.

In one embodiment, said feedback indicator is utilized as a pixel command in determining a pixel illumination area within a pixel array. Referring to said example, said feedback indicator may be indicated by means of illuminating/altering a portion of the displayed image, e.g. red light, a circle or something similar within said obtained position where the quality of the food processing was lacking. In an embodiment, said intensifier is utilized as a magnification/intensification of said pixel command indicating an enlargement of said illumination area within said pixel array. Referring to previous example, this may be visualized by enlarging and/or intensifying said illuminated region, e.g. enlarging said circle within the pin bone area.

In one embodiment, in case no undesired objects are detected within the same or similar position as for said processed food product in a subsequent processed food product processed by said operator, a de-intensifier is triggered indicating a decrement of said feedback. In that way, the operator or the plant manager may in a positive way be informed that improvement is taking place in the food processing for this particular operator. In an embodiment, said de-intensifier is utilized as a de-magnification of said pixel command indicating a decrement of said illumination area within said pixel array. Referring to said example, this may be performed by visually decreasing the circle therefore immediately informing e.g. the operator that improvement is taking place.

In one embodiment, said at least one acquired image data comprises image data acquired from one or more of the following: X-ray data acquired from an X-ray apparatus, 2 Dimensional (2D) digital data acquired from a 2D digital device, 3D digital data acquired form a 3D digital device. This should however not be construed as being limited to said image device, other image device well known to a person skilled in the art may of course also be implemented.

In one embodiment, the method further comprises associating Identification Data (ID) of said operator to said feedback indicator. In that way, it is possible for e.g. a plant manager to monitor individual operators over time and get a processing history for the individual operators. This data may e.g. then be utilized to evaluate the level of training that individual operators need.

A typical implementation of said method is within a processing plant where incoming food products are received by an infeed conveyor to individual operators arranged along the infeed conveyor. The operators have login ID to the processing stations so that all processed food products are associated to the individual operators. The food products are automatically assigned to individual operators vie e.g. sweep arms. The food products are processed at the processing stations, released to a take away conveyor (which may be the same as the infeed conveyor). After that the processed food products are conveyed through a detection apparatus that acquires said image data, where the acquired image data are processed as already discussed.

According to a second aspect of the invention, an automatic feedback system is provided configured to provide a feedback data indicating quality of a food processing performed by an operator, comprising:
a detection apparatus for acquiring image data of a processed food product from an operator,
a processor for processing the acquired image data, the processing including:
    detecting whether undesired objects are present in the processed food product,
    determining, in case undesired objects are detected, the position of the undesired objects within the processed food product,
wherein the processor is further configured to utilize the position data in issuing a feedback indicator indicating a position where said detected undesired objects are present within the food product processed by said operator.

A feedback system is thus provided capable of giving an operator or e.g. a plant manager valuable feedback indicating the quality of the food processing for individual operators within a food processing plant.

The processor could be configured to identify a subsequent erroneously processed food product processed by said operator. As discussed relative to the method of the first aspect of the invention, detection of erroneously processed food product from the same operator could support the operator or a supervisor e.g. relative to need for education etc. Herein, the subsequent erroneously processed food product is defined as a food product with an undesired objects positioned within the same or similar position as for said processed food product. Accordingly, the processor is capable of identifying a food product with an undesired object from a specific operator and to identify a subsequent food product from the same operator.

If such a subsequent erroneously processed food product is identified, the processor may generate an intensifier signal. The intensifier signal could be a visual indication, e.g. a light signal, a tactile indication, such as a vibration signal, or an electronic message, e.g. in the form of a text string or similar data string. The intensifier signal makes it possible for the operator or others to identify that a subsequent erroneously processed food product was identified.

The processor may be configured to determine a distance between the food product with an undesired object and a subsequent erroneously processed food product. The distance may indicate how urgent action is needed. If the subsequent erroneously processed food product is very seldom, i.e. if the distance is large, it may not be urgent to react, whereas if the distance is short, urgency may be required.

The processor may e.g. be configured to determine the distance in a number of separating food products. The separating food product is a food product arranged in a row of food products between the food products with an undesired object and the subsequent erroneously processed food product.

In one example, the processor may be pre-programmable for a specific number of separating food products. As an example, the processor may be pre-programmed for 15 separating food products. In that case, if a food product with an undesired object is determined, and after further processing of 20 food products, a subsequent erroneously processed food product is determined, no intensifier signal is generated. If a food product with an undesired object is determined, and after further processing of 12 food products, a subsequent erroneously processed food product is determined, an intensifier signal is generated.

The processor may also be configured to determine the distance in the form of a time interval which separates the food product with an undesired object from the subsequent erroneously processed food product.

In one example, the processor may be pre-programmable for a time interval. As an example, the processor may be pre-programmed for 15 minutes. In that case, if a food product with an undesired object is determined, and after further processing of food products in a time interval of 20 minutes, a subsequent erroneously processed food product is determined, no intensifier signal is generated. If a food product with an undesired object is determined, and after further processing of food products in a time interval of 12 minutes, a subsequent erroneously processed food product is determined, an intensifier signal is generated In one embodiment, said system further comprises a feedback device associated to the operator, where the feedback device is operably connected to a processor (or said processor) and comprises a display, where said feedback indicator is utilized as a pixel command in determining a pixel illumination area within the display. In that way, the operator or e.g. said plant manager may in a very user friendly way be informed where the food processing needs improvements.

The intensifier signal may particularly be constituted by a change in intensity of the pixel illumination, or a change in size of the illuminated area, or a change in color of the illuminated area.

In one embodiment, said detection apparatus comprises one or more of, but not limited to, an X-ray apparatus and wherein said image data comprises X-ray data, imaging device for acquiring 2D and/or 3D image data.

In one embodiment, said food product is processed at a processing station selected from a plurality of processing stations arranged along an infeed conveyor from which the food product is received, and wherein after processing said food product, it is received by a take-away conveyor and conveyed to said detection apparatus where said image data is acquired. Said infeed conveyor and take-away conveyor may in one embodiment be one and the same conveyor.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
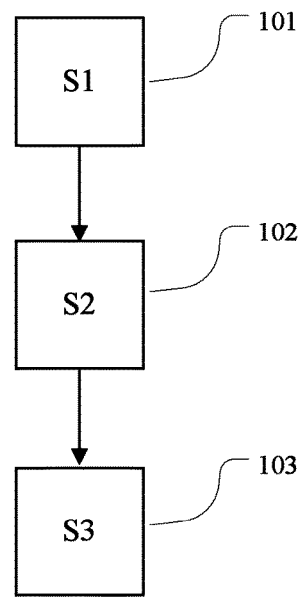
FIG. 1 shows a flowchart of a method according to the present invention of providing a feedback data indicating quality of a food processing performed by an operator, FIG. 2, including FIGS. 2a to 2c and FIG. 3, including

FIG. 1 shows a flowchart of a method according to the present invention of providing a feedback data indicating quality of a food processing performed by an operator.

In step (S1) 101, at least one image data is acquired of a processed food product from an operator. This image data may e.g. include X-ray data, 2 and/or 3 Dimensional image data, or any other type of image data acquired after the food product is processed.

The operator may be arranged at a processing station selected from a plurality of processing stations arranged along an infeed conveyor where e.g. via sweep arms, the food product is automatically moved from the infeed conveyor to the processing station where the operator processes the food product, e.g. removes pin bones from a fish fillet and trims the fish fillet. The food product is then automatically conveyed by e.g. a take-away conveyor through e.g. an inspection apparatus, 2D/3D inspection device or any other type of inspection device.

In step (S2) 102, the acquired image data is processed, where the processing includes at least the step of detecting whether undesired objects are present in the processed food product, obtaining, in case undesired objects are detected, position data of the undesired objects within the processed food product.

In step (S3) 103, the position data is utilized in issuing a feedback indicator indicating a position where said detected undesired objects are present within the food product processed by said operator.

Figure 2:
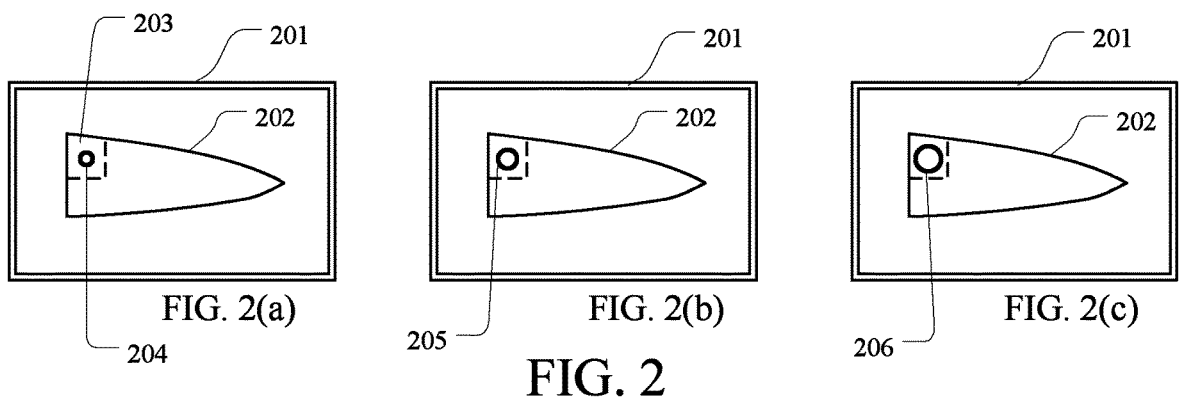

FIG. 2 illustrates one embodiment of issuing such a feedback indicator as discussed in relation to FIG. 1, showing a display 201 that may illustrate outlines 202 of the food product being processed, in the example shown here, the food product is a fish fillet. These outlines may be understood as reference outlines as shown here showing roughly an outer shape of a fish fillet. Another alternative (not shown here) would be to illustrate the outlines of the actual food product based on the subsequent image data.

FIGS. 2a-2c illustrate an embodiment where said feedback indicator is utilized as a pixel command in determining a pixel illumination area within a pixel array in the display 201.

The position data discussed in relation to FIG. 1 is 203, i.e. where undesired objects such as bones was detected, may be area 203. The visual presentation is presented by a pixel array circle 204 (or any other shaped form) indicating via the circle shown here that such an undesired object was detected within area 203. In that way, the operator (or plant manager) may immediately see where the quality of the food processing is lacking.

FIGS. 2b and 2c illustrate an embodiment where undesired objects were detected within the same area 203 in successive food products.

FIG. 2b illustrates an example of lack of quality in the food processing present in one or more subsequent food products within the same area 203. As shown here, an intensifier is triggered that in this case magnifies said pixel command that triggers an enlargement of said illumination area within said pixel array. FIG. 2c shows a further enlargement due to repetitive lack of qualities in the food processing within area 203.

Figure 3:
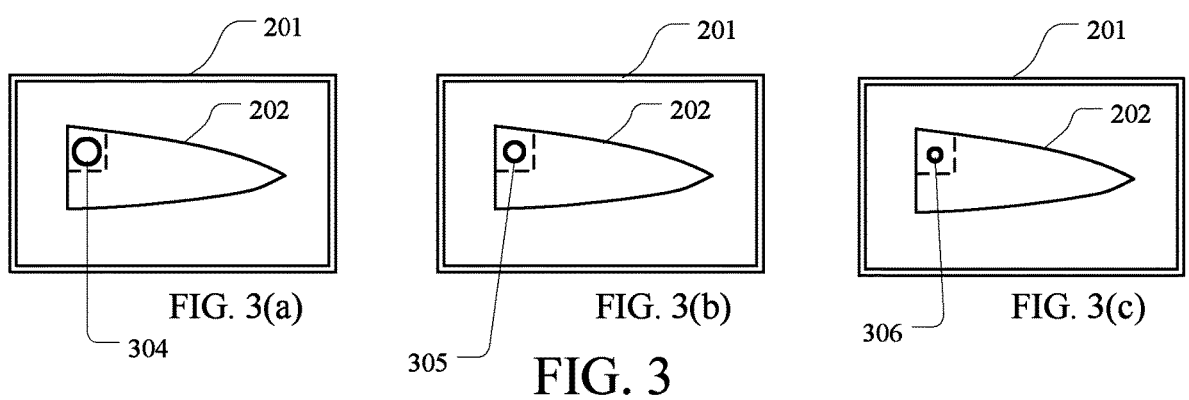
FIGS. 3a to 3c, illustrate one embodiment of issuing a feedback indicator.

FIG. 3 illustrates similar scenario as depicted in FIG. 2, but in this embodiment, an improvement is visible via successively decrease in the pixel array circle 304, 305 and 306, where a de-intensifier is triggered issuing a pixel command indicating a successive decrease in the pixel array because of improvement by the operator.

The display shown in FIGS. 2 and 3 may be a display provided said operator's processing station, which may be among other processing stations arranged along an infeed conveyor, where the food products may be delivered to the processing stations automatically via e.g. a sweep arm or the like, and where the processed food products may subsequently be received by a take-away conveyor, and subsequently conveyed through a detection apparatus, e.g. a digital camera, X-ray apparatus or similar devices well known to a person skilled in the art.

The display 201 may also be arranged at a plant manager that allows the plant manager to monitor the quality of the processing so as to evaluate for example training for individual operators.

Figure 4:
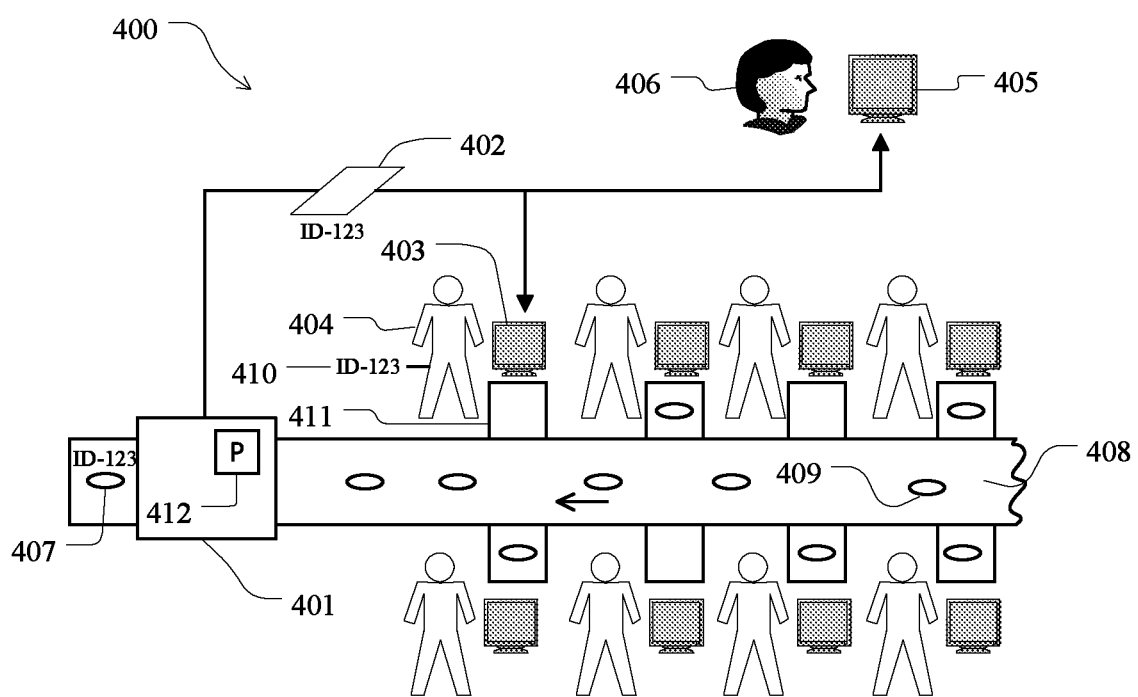
FIG. 4 shows a system according to the present invention for providing a feedback data indicating quality of a food processing performed by an operator.

FIG. 4 shows an embodiment of a system 400 according to the present invention for providing a feedback data indicating quality of a food processing performed by an operator 404, or as shown here is selected from a plurality of operators, stationed along a food processing line comprising an infeed conveyor 408 and an outfeed conveyor, which as shown in this embodiment is the same conveyor as the infeed conveyor.

In operation, incoming food products 409 are conveyed and automatically assigned to a selected processing station available, where the food product is processed. The processing may e.g. include among other things removing fat, undesired tissues, cartilage and bones. After processing the food products, they are placed back on the same conveyor (typically in an automatic way) such that they do not overlap with food products on the conveyor 408 (another takeaway conveyor may also be used, being different from the infeed conveyor).

As an example, an operator 404 who has logged in to a processing station 411 via an unique Identification Code "ID-123" 410 has processed a food product 407.

In the embodiment shown here, the food product 407 has the ID-123 associated to it via tracking the food product as it passed through a detection apparatus, e.g. an X-ray apparatus or any type of detection mechanism used in the food industry.

The image data are processed by a processor 412, e.g. a processor comprised in the detection apparatus 401, where the processing comprises detecting whether undesired objects are present in the processed food product. If undesired objects are detected, the position where the undesired objects are present within the processed food product is determined, similar as discussed in relation to FIGS. 1-3.

The processor is further configured to utilize the position data along with the associated ID data in issuing a feedback indicator 402 indicating a position where said detected undesired objects are present within the food product processed by said operator.

The feedback indicator may then, similar as discussed in relation to FIGS. 2 and 3, be utilized in visually displaying on a display 403 associated with the operator 404 where the quality of the processing was lacking and/or this data may be presented to a plant manager 406 on a display 405 where improvements are needed. Based on this information, the plant manager 406 has an overview over how the different operators with different ID's are performing and react on that by e.g. additional training.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A method of providing a feedback data indicating quality of food processing performed by an operator, comprising the following steps:
    acquiring at least one image data of a processed food product from an operator; and then
    processing the at least one image data, the step of processing including:
        detecting whether undesired objects are present in the processed food product;
        obtaining, in case the undesired objects are detected, position data of the undesired objects within the processed food product;
    utilizing the position data in issuing a feedback indicator indicating a position where said detected undesired objects are present within the food product processed by said operator;
    wherein in case undesired objects are detected in a subsequent processed food product processed by said operator, where the undesired objects are positioned within the same or similar position as for said processed food product, an intensifier is triggered indicating an increase in magnitude of said feedback indicator;
    wherein in case no undesired objects are detected within the same or similar position as for said processed food product in a subsequent processed food product processed by said operator, a de-intensifier is triggered indicating a decrement of said feedback.

2. The method according to claim 1, wherein said feedback data is visually shown to the operator via a display.

3. The method according to claim 1, wherein visually showing said feedback data comprises showing said feedback data within outlines of a food product being processed.

4. The method according to claim 1, wherein said feedback indicator is utilized as a pixel command in determining a pixel illumination area within a pixel array.

5. The method according to claim 4, wherein said intensifier is utilized as a magnification of said pixel command indicating an enlargement of said pixel illumination area within said pixel array.

6. The method according to claim 4, wherein said pixel illumination areas are indicated within a reference contour profile indicating the contour of said food products.

7. The method according to claim 1, wherein said de-intensifier is utilized as a demagnification of said pixel command indicating a decrement of said pixel illumination area within said pixel array.

8. The method according to claim 1, wherein said at least one acquired image data comprises one or more of the following:
    X-ray data acquired from an X-ray apparatus;
    2 Dimensional digital data acquired from a 2D digital device;
    3D digital data acquired form a 3D digital device.

9. The method according to claim 1, further comprising associating Identification Data of said operator to said feedback indicator.

10. An automatic feedback system configured to provide a feedback data indicating quality of a food processing performed by an operator, comprising:
    a detection apparatus for acquiring image data of a processed food product from an operator;
    a processor for processing the image data that is acquired by the detection apparatus, the processing including:
        detecting whether undesired objects are present in the processed food product;

determining, in case undesired objects are detected, the position of the undesired objects within the processed food product;

wherein the processor is further configured to utilize the position data in issuing a feedback indicator indicating a position where said detected undesired objects are present within the food product processed by said operator;

wherein the processor is configured to identify a subsequent erroneously processed food product processed by said operator, wherein the subsequent erroneously processed food product is a food product with an undesired objects positioned within the same or similar position as for said processed food product;

wherein the processor is configured to determine a distance between a food product with an undesired object and a subsequent erroneously processed food product.

11. The automatic feedback system according to claim 10, wherein the processor is configured to generate an intensifier signal in response to the identification of the subsequent erroneously processed food product, the intensifier signal identifying that a subsequent erroneously processed food product was identified.

12. The automatic feedback system according to claim 10, wherein the processor is configured to determine the distance in a number of separating food products, a separating food product being a food product arranged in a row of food products between the food products with an undesired object and the subsequent erroneously processed food product.

13. The automatic feedback system according to claim 10, wherein the processor is configured to determine the distance in the form of a time interval separating the food product with an undesired object and the subsequent erroneously processed food product.

14. The automatic feedback system according to claim 10, further comprising a feedback device associated to the operator, where the feedback device is operable connected to the processor and comprises a display, where said feedback indicator is utilized as a pixel command in determining a pixel illumination area within the display.

15. The automatic feedback system according to claim 14, wherein the intensifier signal is constituted by a change in intensity of the pixel illumination, or a change in size of the illuminated area, or a change in color of the illuminated area.

16. The automatic feedback system according to claim 10, wherein said detection apparatus comprises an X-ray apparatus and wherein said image data comprises X-ray data, and/or digital imaging device for acquiring 2 Dimensional and/or 3 Dimensional image data of the processed food product.

17. The automatic feedback system according to claim 10, wherein said food product processed at a processing station is selected from a plurality of processing stations arranged along an infeed conveyor from which the food product is received, and wherein after processing said food product, the food product is received by a take-away conveyor and conveyed to said detection apparatus where said image data is acquired.

* * * * *